United States Patent [19]
Van Wagoner

[11] Patent Number: 5,150,169
[45] Date of Patent: Sep. 22, 1992

[54] METHOD AND APPARATUS FOR SENSING AND MEASURING RELATIVE POSITION AND MOTION BETWEEN TWO POINTS

[75] Inventor: Earl Van Wagoner, West Jordan, Utah

[73] Assignee: Hoggan Health Industries, Inc., Draper, Utah

[21] Appl. No.: 763,943

[22] Filed: Sep. 23, 1991

[51] Int. Cl.⁵ ............................................. A61B 5/05
[52] U.S. Cl. ..................................... 356/1; 356/373; 356/375
[58] Field of Search ............................ 356/1, 373, 375

[56] References Cited

U.S. PATENT DOCUMENTS

| | | |
|---|---|---|
| 3,712,716 | 1/1973 | Cornsweet et al. |
| 3,908,279 | 9/1975 | Yoslow et al. |
| 4,036,213 | 7/1977 | Gregory |
| 4,182,316 | 1/1980 | Nilsson et al. |
| 4,197,855 | 4/1980 | Lewin |
| 4,303,077 | 12/1981 | Lewin et al. |
| 4,339,954 | 7/1982 | Anson et al. |
| 4,436,099 | 3/1984 | Raftopoulos |
| 4,447,207 | 5/1984 | Kataoka et al. |
| 4,459,109 | 7/1984 | Radke |
| 4,485,825 | 12/1984 | Domjan et al. |
| 4,492,236 | 1/1985 | Pile |
| 4,495,952 | 1/1985 | Klett |
| 4,528,990 | 7/1985 | Knowles |
| 4,586,515 | 5/1986 | Berger |
| 4,600,012 | 7/1986 | Kohayakawa et al. |
| 4,649,934 | 3/1987 | Fraser et al. |

Primary Examiner—Mark Hellner
Attorney, Agent, or Firm—Mallinckrodt & Mallinckrodt

[57] ABSTRACT

Apparatus for measuring relative movement between two points which represents relative movement between two items or between two parts of the same item includes a radiation source such as a light source which generates three orthogonal light beams appearing to originate at a common point, said common point constituting one of the two points, and the light source being secured to one of the items or parts of an item. A radiation sensor capable of detecting in three two-dimensional sensing planes the position of each of the three orthogonal radiation beams, such as three light sensing arrays arranged in three orthogonal planes, each of the three orthogonal sensing planes intersecting at an origin point which constitutes the other of the two points is secured to the other item or part of an item. A calculation unit such as a microprocessor is provided for calculating the relative position of the two points at any particular time from the determined positions of the three radiation beams striking the sensing means at that time and may also be programmed to relate the relative position of the two points and changes in such relative position to the relative position and changes of the two items or parts of an item to which the radiation source and sensor are secured. The movement between the two points, the two items, or parts of the same time is determined by calculating the difference in positions between two measured relative positions.

23 Claims, 6 Drawing Sheets

FIG. 3
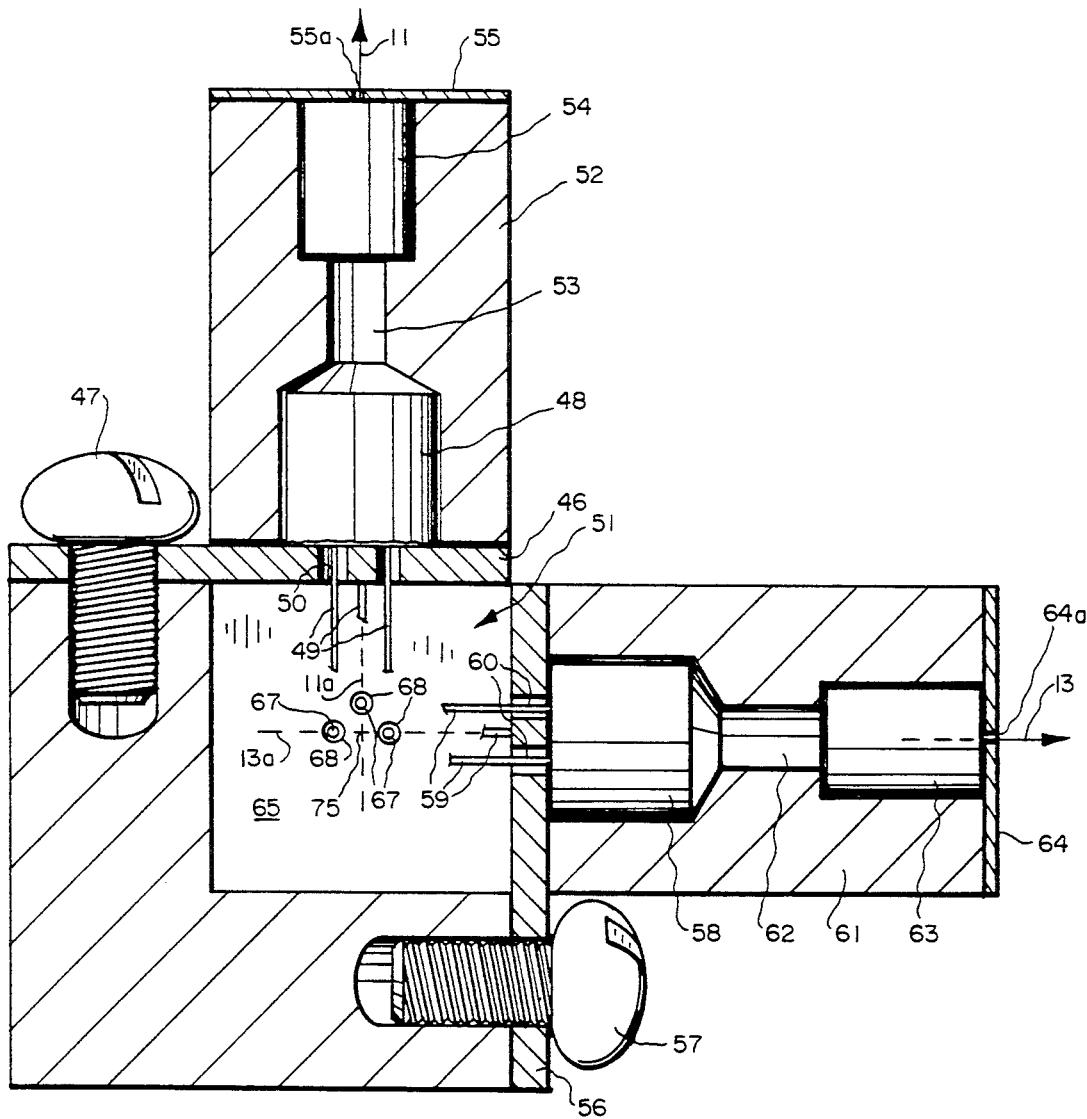
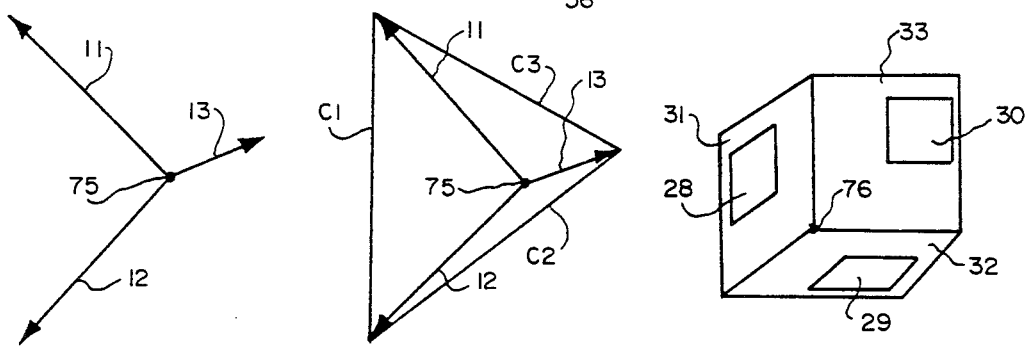
FIG. 4    FIG. 5    FIG. 6

METHOD AND APPARATUS FOR SENSING AND MEASURING RELATIVE POSITION AND MOTION BETWEEN TWO POINTS

BACKGROUND OF THE INVENTION

1. Field

The invention is in the field of measuring relative motion between two points, such as between two separate items or between two parts of the same item, and particularly, accurately measuring small amounts of such relative motion.

2. State of the Art

Various devices and methods have been developed for measuring relative motion between two items or between two parts of the same item. Most of these are limited to measuring relative motion in a limited number of directions or planes. For example, relative motion may be measured in a single direction for items which move toward or away from one another by measuring the distance between the points at any particular time by using measuring equipment such as rulers or calipers. Such measuring equipment does not work where the relative movement to be measured occurs or may occur in several dimensions, or where measurements are to be taken during movement. In measuring relative movement of various body parts or in measuring relative movement of two parts of a item when the item is subjected to strain or stress, specialized measuring equipment is required.

Several devices have been developed to measure movement of the jaw and mandibular joint which use light sources and light detectors to sense such movement. U.S. Pat. No. 4,447,207 shows three light sources with three associated detectors. The three light sources are spaced in fixed relationship and attached to move with the jaw of the user as the jaw is moved in relation to the user's head. The detectors are held fixed with a user's head and measure the linear movement of the light sources in two dimensional planes as the jaw is moved relative to the head. The measurements are not used to actually measure relative movement between the jaw and head, but are used to reproduce in a model joint the same movement as detected in the movement of an actual jaw.

U.S. Pat. No. 4,496,952 shows a device for measuring jaw movement wherein movement of the jaw is transmitted to a measuring device including a plurality of light sources and an equal plurality of light position sensors. In several embodiments, three light sources generate three mutually orthogonal, but offset beams of light. These beams are directed to three mutually orthogonal reflecting grids. Light sensors are located adjacent the light sources and receive light reflected from the light reflecting grids. The sensors generate pulses, the number of pulses generated being proportional to the movement of a light beam in one dimension along the grid. In another embodiment, two mutually orthogonal, but offset, light beams are generated and directed to two orthogonal sensing devices which sense the position and movement of each beam in two dimensions. The patent teaches that three dimensional movements can be measured using three one dimensional grids, or using two two dimensional grids. However, the device of U.S. Pat. No. 4,495,952 will measure only translational movement in three dimensions, it will not account for rotational movement of the light sources and, if rotational movement occurs, it will provide incorrect measurements of movement and position of the light sources. Thus, the device of U.S. Pat. No. 4,495,952 can be used only where steps are taken to insure that no rotational movement is present.

In many areas of mechanical testing it is desired to measure relative movement between two items or to measure the relative movement between two parts of the same item. The relative movement usually occurs in three dimensions and includes rotational movement within those three dimensions. There is currently no apparatus or method known to the inventor for accurately measuring the relative movement where completely unrestrained three dimensional relative movement between two points is allowed. Such measurement would be desirable in many testing situations. For example, arthrodesis, a procedure for treating spinal back problems by causing the vertebra to grow together or fuse to form an immobile joint or unit, is a common orthopedic procedure. It is generally thought to be important to immobilize the vertebra involved to allow the vertebra to fuse. If excessive relative motion between the two vertebra occurs, the vertebra may not successfully fuse. In order to maintain an immobilized or motionless state during the healing or fusing process, it is usual practice to implant an immobilization device and secure it to appropriate vertebra. The purpose of the immobilization device is to keep the adjacent vertebra to be fused motionless until the two vertebra have fused. However, it has been difficult to test such immobilization devices to determine their real effectiveness. Strength and failure testing on the devices themselves do not indicate how well they actually perform to immobilize the attached or intermediate vertebra. Past testing of immobilization devices affixed to cadaver spinal columns have been useful in determining the effectiveness of the attachment of the device to the vertebra, but have not been effective in measuring the effectiveness in actually immobilizing specific vertebra. This is because relative motion of the vertebra has been impossible to accurately measure with existing measuring devices. Similarly, unrestrained, three-dimensional relative movement has been difficult to accurately measure in various other biomechanical, mechanical, or stress or strain analysis situations.

SUMMARY OF THE INVENTION

According to the invention, unrestricted, three dimensional relative movement between two items or parts of an item may be accurately determined by attaching a radiation source which produces three orthogonal beams of radiation effectively originating at a single point to one of the items and attaching to the other item a radiation sensitive position sensing device arranged to detect the position of each of the three orthogonal radiation beams. The radiation sensitive position sensing device senses the position of each of the radiation beams in one of three different sensing planes. The three sensing planes are orthogonal to one another and intersect at an origin point. The sensing device may take the form of three individual detectors, each detector capable of detecting in two dimensions the position of a radiation beam striking the detector. The three detectors are arranged in the three orthogonal sensing planes and are mounted so that each detector intersects one of the three radiation beams and senses the position of the radiation beam striking it. The radiation source can include three separate radiation beam generators each generator arranged to generate one of the radiation beams and arranged with respect to one another so that the three radiation beams appear to emanate from the same point.

As indicated above, the three radiation beams appear to originate at a common point. This means, depending upon the arrangement of the radiation source, that the three beams will all intersect at a common point, or, as will usually be the case, if the beams are projected back through the beam generators, the projections of the beams will all intersect at a common point. Thus, it can be said that the directional vectors of the three beams all intersect at a common point. Also as indicated above, the sensors are arranged to sense radiation in three orthogonal planes. These planes intersect at an origin point. The relative positions and movement sensed and determined by the apparatus is the relative positions and movement of the common point and the origin point. The calculation means will generally be a microprocessor or computer programmed to calculate the relative positions of the common point and the origin point at any particular time based on the sensed positions of the three radiation beams.

In a presently preferred embodiment of the invention, the radiation source is a light source, either visible or infrared, which produces three light beams. The light source may include three laser diodes with each diode generating one of the light beams. The sensing means include three detectors which each include a plurality of light sensing elements arranged in a two dimensional grid so that the specific elements upon which a light beam fall are energized or assume a different state than the nonilluminated elements of the grid. In this way, the position of the light beam striking the grid is determined or sensed. The detectors may each be an integrated array of light sensing elements known as a charge coupled device. It is presently preferred that the light beam be of a diameter to strike a plurality of the light sensing elements of the array and that the calculation circuitry determine the position of the light beam by calculating the position of the center of the light beam. In this way, the position of the beam can still be accurately determined even if a specific light sensing element upon which the light beam falls is defective.

The structural arrangement of the three orthogonal radiation beams so that they appear to originate at a common point and the structural arrangement of the three orthogonal sensing planes so that they intersect at an origin point, allow the radiation beams to be mathematically represented as a right tetrahedron with one apex being the apparent common point of origination of the light beams and the remaining apices being the points of intersection of the light beams with the sensing planes. This allows the position of the apparent common point of origination of the light beams with respect to the origin point of the sensor planes to be accurately calculated.

The method of the invention involves generating three orthagonal radiation beams appearing to originate at a first point and providing a sensing means capable of detecting radiation beams in three orthagonal, two dimensional sensing planes with each of the three sensing planes intersecting at a second point. The position of the first point with respect to the second point and the relative movement between the two points may be determined by positioning the radiation source with respect to the sensing means so that respective radiation beams will fall on respective sensing planes over the expected extent of relative movement to be measured between the two points. By determining the positions where each of the radiation beams intersect respective sensing planes, the relative position of the first and second points may be determined for any relative position of the two points. By determining the difference in relative positions of the two points between any two relative positions, the relative movement of the two points between the two relative positions may be determined.

The position of first point with respect to the second point, wherein both translational positions as well as rotational orientation is considered, may be mathematically calculated by using the three radiation beams to form a right tetrahedron with one apex of the tetrahedron formed by the first point and the remaining three apices of the tetrahedron formed by the points of intersection of the radiation beams with the respective sensing planes. The orientation of the tetrahedron with respect to the orthogonally arranged sensors is indicative of the orientation of the first point with respect to the second point. The respective coordinates of the first point with respect to the second point are indicative of the translational position of the first point with respect to the second point and of the distance between the two points. In this way, the determined positions of the two points can take into account all degrees of freedom of movement between the two points and the determination of movement between two measured relative positions of the two points takes into account and indicates not only translational relative movement between the two points, but relative rotational movement as well.

THE DRAWINGS

The best mode presently contemplated for carrying out the invention is illustrated in the accompanying drawings, in which:

FIG. 1, is a perspective view of an apparatus of the invention secured to vertebra of a spinal column to measure relative movement of two adjacent vertebra;

FIG. 2, a side elevation of the apparatus of FIG. 1;

FIG. 3, a horizontal section taken on the line 3—3 of FIG. 2 and rotated 180°;

FIG. 4, a diagrammatic representation of the radiation beams of the apparatus;

FIG. 5, a diagrammatic representation similar to FIG. 4, but showing the ends of the radiation beams connected to form a right tetrahedron;

FIG. 6, a diagrammatic representation of the sensor planes of the apparatus;

FIG. 7, a combination or superposition of the radiation beams and sensor planes of FIGS. 5 and 6, but labeled somewhat differently, along with a differently positioned set of radiation beams shown in broken lines;

FIG. 8, a diagrammatic representation of the solid line showing of FIG. 7, but showing additional lines illustrative of portions of calculations described as an example of calculations usable with the invention;

FIG. 9, a diagrammatic representation illustrative of example calculations;

FIG. 10, a diagrammatic representation illustrative of example calculations;

FIG. 11, a diagrammatic representation of a single one of the planes of FIGS. 7–10 illustrative of example calculations;

FIG. 12, a diagrammatic representation of the plane of FIG. 11 illustrative of example calculations;

FIG. 13, a diagrammatic representation of the plane of FIG. 11 illustrative of example calculations; and FIG. 14, a block diagram of portions of the apparatus of the invention.

DETAILED DESCRIPTION OF THE ILLUSTRATED EMBODIMENT

Figure 1:
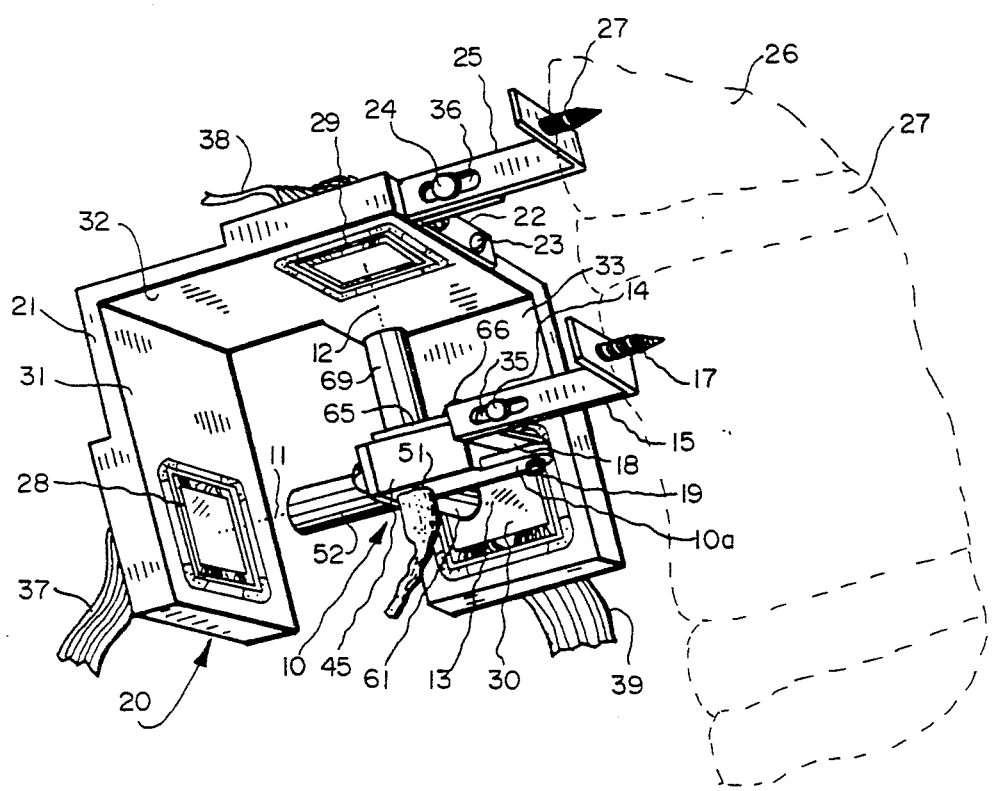
Figure 2:
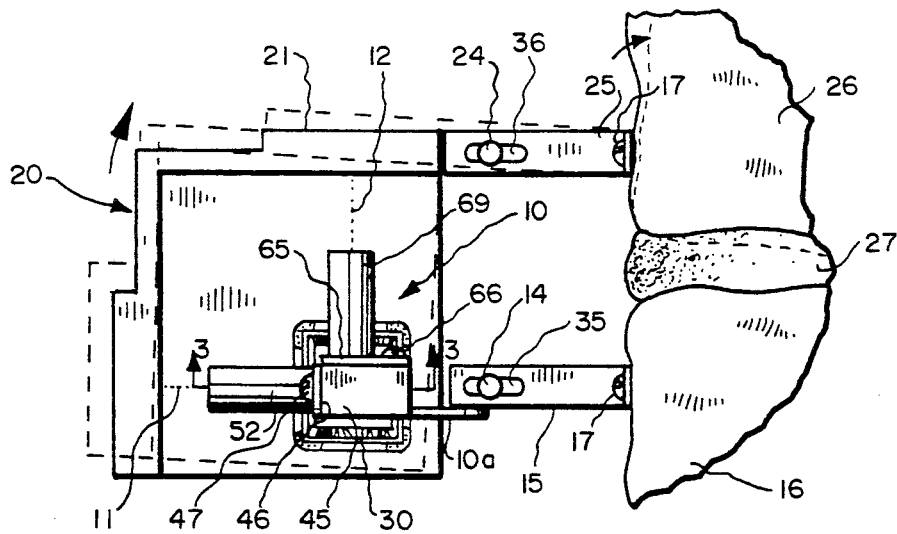

The apparatus of the invention is shown and specifically described as installed on a cadaver spinal column so movement of adjacent vertebra can be measured. This is merely an example of a use of the measuring apparatus of the invention as it can be used anytime relative movement between two items or between two parts of the same item is to be measured. Referring to FIGS. 1 and 2, a radiation source, which in the preferred embodiment shown takes the form of a light source indicated generally as 10 adapted to produce three orthogonal light beams 11, 12, and 13, is secured by screw 14 to mounting arm 15 which is secured to vertebra 16 by screw 17. Securement to mounting arm 15 is through bracket 18 secured to light source mounting tab 10a by screw 19. A radiation sensor, which in the preferred embodiment shown takes the form of a light sensor indicated generally as 20, includes a base member 21 with mounting bracket 22 secured thereto by screws 23. Mounting bracket 22 is secured by screw 24 to mounting arm 25 secured to vertebra 26 by screw 27. In this manner, light source 10 is secured to vertebra 16 and light sensor 20 is secured to adjacent vertebra 24. A vertebral disc 27 is shown in normal position between the adjacent vertebra 16 and 26. Light sensor base member 21 has light detectors 28, 29, and 30 mounted in base member faces 31, 32, and 33, respectively, which are configured so that faces 31, 32 and 33 each form a plane, with the planes formed being orthogonal to one another.

Once the light source 10 and light sensor 20 are mounted on the respective vertebra 16 and 26, the relative positions of the light source 10 and light sensor 20 are adjusted so that the light beams 11, 12, and 13 generated by the light source 10 each fall on a light detector. Proper positioning is as illustrated in FIG. 1, where light beams 11, 12, and 13 fall on light detectors 28, 29, and 30, respectively. To facilitate this adjustment, support arms 15 and 25 are provided with slots 35 and 36, respectively, which allow longitudinal adjustment along the mounting arms. Rotational adjustment movement is also allowed about screws 14, 19, and 24. Adjustment is made so that, in normal position, each of the light beams falls on a desired location of the respective detectors. Thereafter, relative movement of the light sensor 20 with respect to the light source 10 caused by movement of the structure being tested will cause movement of the respective light beams across their associated light detectors. For example, if the spinal column being tested is flexed to cause vertebra 26 to move to the position shown in broken lines in FIG. 2, light sensor 20 moves to the position also shown in broken lines. This will cause the respective light beams 11, 12, and 13 to intersect light detectors 28, 29, and 30 at different locations than at the position shown in solid lines. This change in the location where the light beams intersect the light detectors serves as the basis for detecting and measuring relative movement of the adjacent vertebra, or of any other structure or item to which the apparatus is secured.

Various types of light detectors may be used in the apparatus. For detecting very small relative movements, arrays of charge coupled devices have been found satisfactory. A preferred array is rectangular in shape with a size of 8.8 × 11.4 mm and with an array size of 380 × 488 sensing elements providing a total of 185,440 sensing elements. With such an array and using a collimated laser beam, movement as small as about 30 microns can be detected and measured. Such an array is sold by Fairchild Weston Systems, Inc. of Sunnyvale, Calif., under the designation CCD222. The resolution of movement that can be measured is dependent upon the size of the particular array sensing elements used. Arrays having smaller sensing elements can be used to provide greater resolutions. However, currently available arrays with smaller sensing elements are more expensive than the specific array indicated so the array used will depend upon a balancing of the resolution desired and cost of the sensing arrays. The detectors 28, 29, and 30 are mounted in the base member 21 so that the electrical conductors 37, 38, and 39, respectively, extend from the back faces of the base member and are connected to a calculation means which also includes control circuitry for the detectors.

The light source 20 preferably includes three laser diodes, such as aluminum gallium arsenic (AlGaAs) diodes arranged to generate the three light beams. As shown in FIG. 1–3, the light source 10 includes a base member 45. A diode mounting plate 46 is attached to base member 45 by screw 47. Laser diode 48, FIG. 3, is mounted on mounting plate 46 with the three diode leads 49 extending into recess 51 through holes 50 in mounting plate 46. In most cases, the laser diodes are supplied commercially as a unit with the mounting plate already attached. A diode cover 52 is fitted over diode 48 to provide a collimating passage 53 for the light from the diode. A collimating lens 54 is glued in place in the enlarged end of passage 53. An end plate 55 with pin hole 55a is secured to the end of cover 52. This provides a narrow, collimated light beam 11 emanating from the end of diode cover 52. The diameter of the light beam 11 is determined by the diameter of pin hole 55a.

A second diode mounting plate 56, FIG. 3, is attached to base member 45 by screw 57. Laser diode 58 is mounted on mounting plate 56 with the three diode leads 59 extending into recess 51 through holes 60 in mounting plate 56. Diode cover 61 is fitted over diode 58 to provide a collimating passage 62 for the light from the diode. A collimating lens 63 is glued in place in the enlarged end of passage 62. An end plate 64 with pin hole 64a is secured to the end of cover 61. This provides a narrow, collimated light beam 13 emanating from the end of diode cover 61. The diameter of the light beam 13 is determined by the diameter of pin hole 64a.

Similarly, a third diode mounting plate 65, FIGS. 1 and 2, is attached to base member 45 by screw 66. A laser diode, not shown, is similarly mounted on mounting plate 65 with the three diode leads 67 extending into recess 51 through holes 68, FIG. 3, in mounting plate 65. Diode cover 69, FIGS. 1 and 2, covers the diode on mounting plate 65 and similarly has a collimating passage, collimating lens, and end plate with pin hole to provide a narrow, collimated light beam 12.

While the size of the pin holes, such as 55a and 64a in plates 55 and 64, respectively, can vary, depending upon a number of factors such as the detectors used and the desired resolution of measurement, a hole the size of eight-one-thousandths (0.008) to ten-one-thousandths (0.010) of an inch has been found satisfactory. Ideally, the best resolution would be obtained using a light beam of diameter to illuminate a single sensing element at a time. With such a light beam, the particular sensing element illuminated by the light beam at any time would accurately show the position of intersection of the light beam and the sensor array. A further advantage of a small diameter beam is that although the beams are collimated as much as possible, complete collimation has not yet been achieved so the beam has some tendency to enlarge or defocus as the source of the beam moves farther away from the sensor. The smaller the beam, the less the significance of this effect. Perfect sensor arrays are expensive and arrays with some defective sensing elements are commercially available at more reasonable cost. However, a defective sensing element in an array is difficult to compensate for if the beam covers only a single sensing element. If the beam is of a diameter to cover several sensing elements, a defective sensing element can be compensated for. The particular sensor array identified above has sensing elements arranged in rows and columns one-thousandth (0.001) inch wide. With a hole diameter of 0.008 inch which produces a light beam of 0.008 inch diameter, the light beam will have a diameter equal to eight (8) individual sensing elements. Thus, when the light beam strikes the sensor array, a plurality of individual sensing elements are illuminated by the light beam. Because of this, movement of the light beam in relation to the sensor array causes a change in state of several individual sensing elements. This, in turn, allows accurate movement measurement even if a particular sensing element upon which light falls is defective and does not produce an output. The calculation electronics, which also controls operation of the sensing arrays, can be programmed to determine the number of individual sensing elements illuminated and determine the position of the center of illumination which is used to indicate the position of the light beam. This allows a grade of sensor array less than perfect to be used in the invention which currently substantially reduces the cost of the array. It is presently preferred that the sensor array used have one dimension with no adjacent defective sensing elements.

It is important in the apparatus and method of the invention that the light beams 11, 12, and 13 all appear to originate from a common point or common source. As illustrated and described, the light beams do not actually emanate from a single source at a single point, but the separate laser diodes which generate the separate light beams are arranged so the beams appear to emanate from a single point. This means that the projection of each light beam back through the diode intersects in a common point. Alternately stated, the directional vector of each light beam will intersect in a common point. As shown in FIG. 3, if light beam 11 were extended back through the diode 48, it would follow the straight path indicated by broken line 11a. Similarly, if light beam 13 were extended back through the diode 58, it would follow the straight path indicated by broken line 13a. These two lines intersect at point 75. The diode and diode cover 69 which forms light beam 12 are positioned so that if light beam 12 were extended back through the diode, it too would pass through point 75. Thus, all three light beams appear to originate at the common point 75 and to extend orthogonally outwardly therefrom. This is shown diagrammatically in FIG. 4. If the ends of the representations of the beams 11, 12, and 13 in FIG. 4 are connected by lines $C_1$, $C_2$, and $C_3$, as shown in FIG. 5, a right tetrahedron is formed. Of course, various other arrangements of light sources, or even a single light source at point 75, could be used to generate the light beams so that they all appear to, or actually do, emanate from a single point 75.

Further, as indicated with respect to the sensor 20, sensor base member 21 provides three orthogonally arranged planes, indicated as faces 31, 32, and 33 for mounting of the detectors 28, 29, and 30, respectively. As thus mounted, the detectors provide three mutually orthogonal sensor planes, which are shown to coincide with the base member faces 21, but could be displaced therefrom. These sensor planes and detectors are shown diagrammatically in FIG. 6. It is important to note that these three sensor planes intersect at an origin point 76. Applicant has found that when the light beams effectively emanate from a common point and when the detectors ar arranged in orthogonal planes that intersect at a common point, it is mathematically possible to determine the position of one of the points with respect to the other by determining the position at which each light beam intersects its associated sensor plane. Such positions can be expressed in terms of coordinates in the respective planes. The coordinates are easily obtained from the detector grids, i.e., the sensing element arrays. These measured coordinates uniquely determine the position of one point with respect to the other. Relative position of one point with respect to the other contemplates determination of both relative lateral positions as well as rotational positions and allows determination of the change of position of the two points to take into account rotational as well as translational relative movement.

Figure 7:
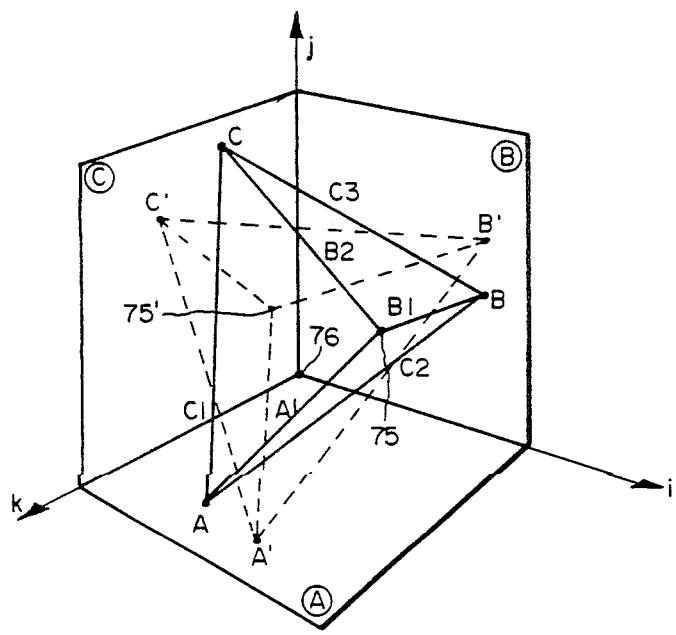
Figure 14:
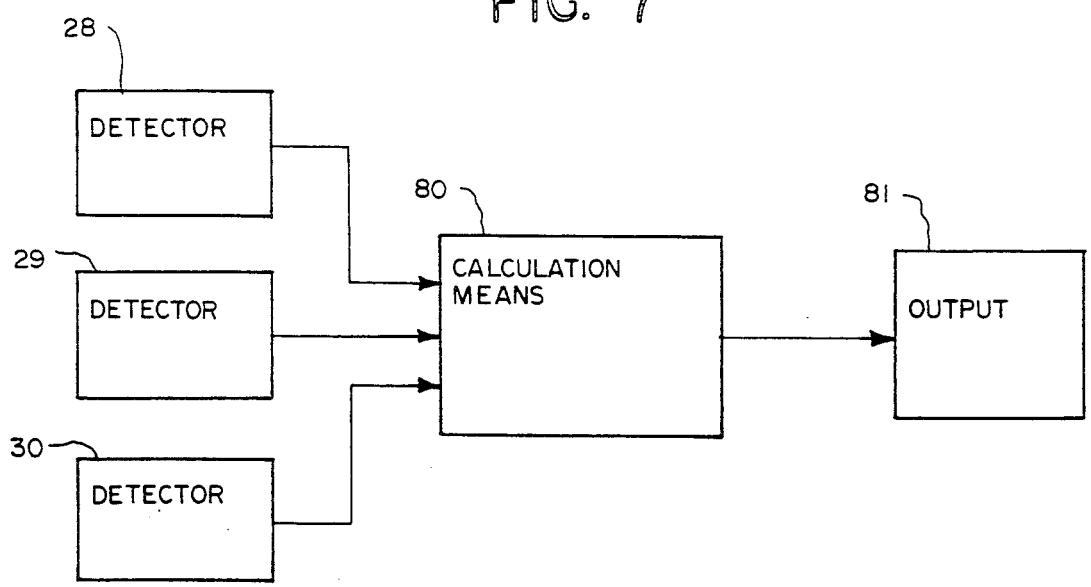

FIG. 7 is a diagrammatic combination or superposition of FIGS. 5 and 6, but not showing the specific detectors of FIG. 6. As indicated, since they appear to originate from a single source, the three orthogonal collimated light beams form a right tetrahedron, with the light source at the apex 75 where the three mutually orthogonal sides of the tetrahedron meet. The apex of the tetrahedron 75 in FIG. 7 is defined by the intersection of lines $A_1$, $B_1$, and $B_2$, which correspond to the light beams 12, 13, and 11 respectively, as shown in FIGS. 4 and 5. The tetrahedron faces the sensor represented as a set of three mutually orthogonal sensor planes, plane A, plane B, and plane C corresponding to sensor planes 32, 33, and 31 respectively, of FIG. 6, which intersect in origin 76. The line of intersection of sensor planes A and B is labeled i, and forms the i or x axis, the line of intersection of sensor planes B and C is labeled j, and forms the j or y axis, and the line of intersection of sensor planes A and C is labeled k, and forms the k or z axis. The other three apices of the tetrahedron are at the points A, B, and C where the respective light beams represented by $A_1$, $B_1$, and $B_2$ intersect the sensor planes represented by plane A, plane B, and plane C. These points can be represented by the coordinates of the points of intersection in the respective planes and are defined, respectively, as $(A_i,A_k)$, $(B_i,B_j)$, and $(C_k,C_j)$. The edges or sides of the tetrahedron are labeled $A_1$, $B_1$, and $B_2$, representing the light beams, and $C_1$, $C_2$, and $C_3$ representing the lines connecting the ends of the light beams, i.e. their points of intersection with the respective sensor planes, represented by points A, B, and C.

Changes in position of point 75 relative to point 76 cause changes in the length of the sides of the tetrahedron, and if rotational changes occur, also cause changes in the orientation of the tetrahedron. These various changes are measured as changes in the coordinates of points A, B, and C by the light detectors in the sensor planes before and after the change. FIG. 7 shows a point 75' displaced from and rotated from point 75 with the changed points of intersection with the respective sensor planes indicated as A, B, and C. As can be seen, the lengths of the various sides of the tetrahedron have changed as has the orientation. To determine the movement that has occurred as the light source moved from point 75 to point 75', the position of point 75 is determined and then the position of point 75' is determined. The difference in position between point 75 and point 75' indicates how much point 75 has moved between the first measured relative position and the second measured relative position. The light detectors determine the coordinates, $(A_i, A_k)$, $(B_i, B_j)$, and $(C_j, C_k)$ at any time and the coordinates sensed are sent to and recorded in the calculation means. The coordinates determined for any relative position of points 75 and 76 can be used to derive the length of the edges of the tetrahedron, $A_1$, $B_1$, $B_2$, $C_1$, $C_2$, $C_3$ for that position.

The formulas for deriving the lengths of the sides of the tetrahedron are shown as follows:

Sides $C_1$, $C_2$, $C_3$ are defined by the following formula:

$$C_1 = \sqrt{(C_j^2 + (C_k - A_k)^2 + A_i^2)}$$

$$C_2 = \sqrt{(B_j^2 + (B_i - A_i)^2 + A_k^2)}$$

$$C_3 = \sqrt{(B_i^2 + (B_j - C_j)^2 + C_k^2)}$$

Each side ($C_1$, $C_2$, and $C_3$) is the hypotenuse of a right triangle. The Pythagorean theorem states the square of the hypotenuse equals the sum of the squares of the two sides. Hence, each hypotenuse is mathematically related to the other sides of its triangle as follows:

$C_1^2 = A_1^2 + B_2^2$     Equation 1:

$C_2^2 = A_1^2 + B_1^2$     Equation 2:

$C_3^2 = B_1^2 + B_2^2$     Equation 3.

By mathematical manipulation of the above three equations, solutions for the three values A, B, and C may be obtained. Solving equation 2 for $B_1^2$ yields:

$$B_1^2 = C_2^2 - A_1^2$$

Rearranging and solving equation 1 for $A_1^2$ and substituting the solution for $A_1^2$ in the above equation yields:

$$B_1^2 = C_2^2 - (C_1^2 - B_2^2).$$

Removing the parentheses gives:

$$B_1^2 = C_2^2 - C_1^2 + B_2^2.$$

Rearranging and solving equation 3 for $B_2^2$ and substituting the solution for $B_2^2$ in the above equation yields:

$$B_1^2 = C_2^2 - C_1^2 + (C_3^2 - B_1^2).$$

Removing the parentheses gives:

$$B_1^2 = C_2^2 - C_1^2 + C_3^2 - B_1^2.$$

Rearranging the equation gives:

$$2B_1^2 = C_2^2 - C_1^2 + C_3^2.$$

Dividing both sides by 2 gives:

$$B_1^2 = \frac{C_2^2 - C_1^2 + C_3^2}{2}$$

Taking the square root of both sides gives:

$$B_1 = \sqrt{\frac{C_2^2 - C_1^2 + C_3^2}{2}}$$

Rearranging equation 1 and taking the square root of both sides gives:

$$A_1 = \sqrt{C_2^2 - B_1^2}$$

Rearranging equation 3 and the taking the square root of both sides gives:

$$B_2 = \sqrt{C_3^2 - B_1^2}$$

As shown in FIG. 7, $A_1$, $B_1$, and $B_2$, denote respectively the lengths between the light source positioned at point 75 and the points of intersection of the respective light beams with the light detectors positioned on planes A, B, and C. $A_1$, $B_1$, and $B_2$, also define the length of three sides of the right tetrahedron, while $C_1$, $C_2$, and $C_3$ define the length of the other three sides of the tetrahedron. The coordinates of the points of intersection of the light beams with the detectors are defined in relation to point 76. The coordinates of point 76 are considered (0,0,0). The coordinates of the points of intersection in combination with and the lengths of $A_1$, $B_1$, and $B_2$, and $C_1$, $C_2$, and $C_3$ provide an indication of the position and orientation of point 75 with respect to point 76. All information necessary to determine relative position and orientation is available and can be utilized in various ways depending upon the reference position and how the relative movement is to be characterized.

If the relative movement between the two points is known to be translational only, i.e., there is no relative rotational movement, the changes in the coordinates of intersection of the light beams with the detectors will generally indicate this translational movement. However, where rotational movement is involved, additional calculations will be necessary to determine if, and to what extent, rotational movement has taken place. The representation of the radiation source as a right tetrahedron allows the orientation of the tetrahedron, and thus the relative orientation of the points 75 and 76, to be calculated from knowledge of the points of intersection and length of the sides of the tetrahedron. The calculations providing the quantitative values of position and orientation can be approached from several standpoints. An example of an approach developed by the inventor which breaks down the relative movement between the two points into the apparent movement in each of the A, B, and C planes is explained below, and illustrated in FIGS. 8-13.

Figure 8:
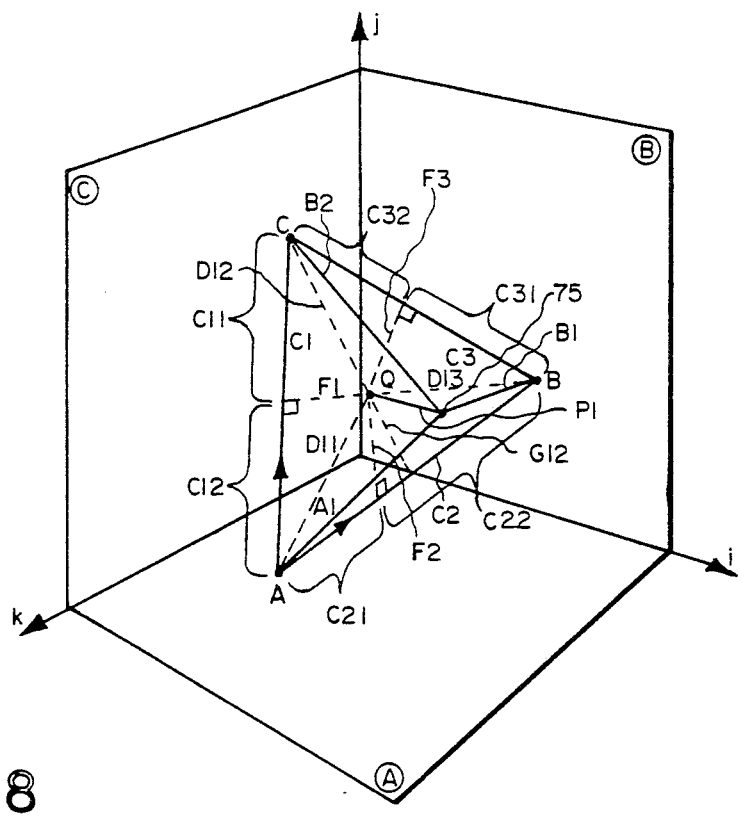

As shown in FIG. 8, the tetrahedron has a base defined by the lines $C_1$, $C_2$, and $C_3$ joining the respective points of intersection of the light beams with the detectors. Thus, line $C_1$ joins points A and C, $C_2$, joins points A and B, and $C_3$ joins points B and C. A line $P_1$ may be drawn from the light source 75, in some instances referred to as point P, to the base, and perpendicular thereto, to intersect the base at point Q. Lines $D_{11}$, $D_{12}$, and $D_{13}$ may be drawn from point Q to the points of intersection A, C, and B, respectively, and lines $F_1$, $F_2$, and $F_3$ may be drawn from point Q to intersect lines $C_1$, $C_2$, and $C_3$, respectively, at right angles. $G_{11}$ in the total length of the line extending from point C through point Q to intersect with the line $C_2$. Thus, $G_{12}$ includes $D_{12}$.

Knowing the values of $A_1$, $B_1$, $B_2$, $C_1$, $C_2$, and $C_3$, as determined above, and using basic trigonometry to solve for various lengths, we find that $$C_{11} = \left(\frac{B_2}{C_1}\right) B_2$$

$$C_{12} = \left(\frac{A_1}{C_2}\right) A_1$$

$$G_{12} = \sqrt{C_1^2 - C_{21}^2}$$

$$D_{12} = \frac{C_{11} 2 G_{12} C_1}{G_{12}^2 + C_1^2 - C_{21}^2}$$

$$P_1 = \sqrt{B_2^2 - D_{12}^2}$$

$$D_{11} = \sqrt{A_1^2 - P_1^2}$$

$$D_{13} = \sqrt{B_1^2 - P_1^2}$$

Figure 9:
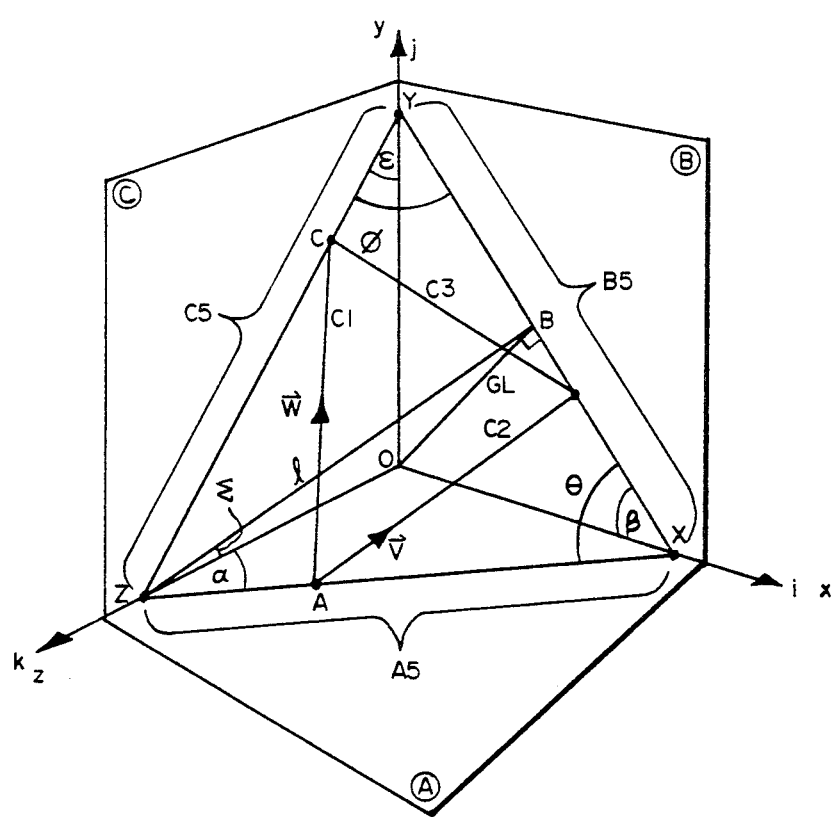

As shown in FIG. 9, the base of the tetrahedron is in a plane that intersects the sensor planes A, B, and C. The plane of the base of the tetrahedron intersects the i axis at point X, intersects the j axis at point Y, and intersects the k axis at point Z. The coordinates of points A, B, and C are:

$$A = (A_i, A_j, A_k)$$

$$B = (B_i, B_j, B_k)$$

$$C = (C_i, C_j, C_k).$$

Also, we can define the lines $C_1$ and $C_2$ as vectors v and w as follows:

$$\vec{v} = \vec{AB}$$

$$\vec{w} = \vec{AC}$$

then:

$$\vec{v} = (B - A) = (B_i - A_i, B_j - A_j, B_k - A_k)$$

$$\vec{w} = (C - A) = (C_i - A_i, B_j - A_j, C_k - A_k).$$

In order to mathematically define the base plane of the tetrahedron it is necessary to define a vector n perpendicular to the base plane:

$$\vec{n} = \vec{v} \times \vec{w}.$$

The equation for the base plane is:

$$\vec{n} \cdot (\vec{x} - \vec{0A}) = 0$$

where $$\vec{x} = (x, y, z)$$

and $$\vec{n} = (n_i, n_j, n_k).$$

Solving:

$$\vec{n} \cdot (\vec{x} - \vec{0A}) = n_i(X - A_i) + n_j(Y - A_j) + n_k(Z - A_k) = 0$$

$$n_i x + n_j y + n_k z = N_i A_i + N_j A_j + N_k A_k.$$

To find the x intercept, set y and z to 0, to find the y intercept, set x and z to 0, and to find the z intercept, set x and y to 0. This gives the coordinates of points X, Y, and Z.

Figure 10:
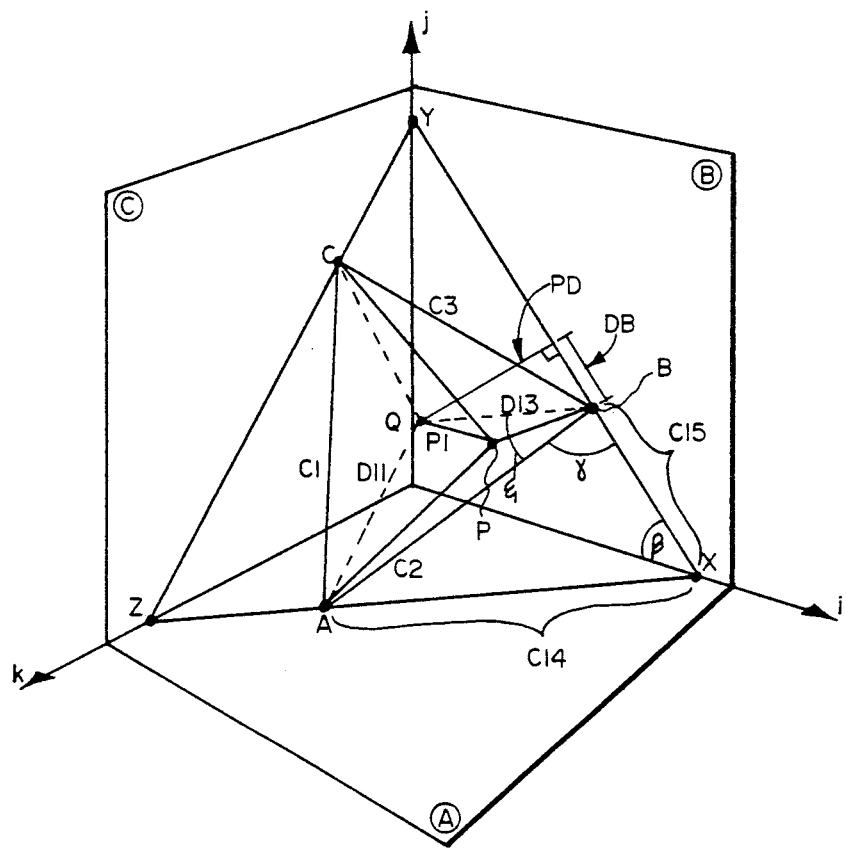

The base plane of the tetrahedron forms a triangle as shown in FIGS. 9 and 10 defined by the lines $\overline{XY}$, $\overline{YZ}$, and $\overline{XZ}$. The length of these lines are:

$$\overline{XY} = \sqrt{X_i^2 + Y_i^2}$$

$$\overline{YZ} = \sqrt{Y_i^2 + Z_i^2}$$

$$\overline{XZ} = \sqrt{X_i^2 + Z_i^2}$$

Line $\overline{XY}$ is labeled $B_5$, line $\overline{YZ}$ is labeled $C_5$, and line $\overline{XZ}$ is labeled $A_5$, FIG. 9. The angles $\beta$, $\alpha$, $\epsilon$, $\phi$, and $\theta$ shown in FIGS. 9 and 10 and the length of l, FIG. 9, can be found as follows:

$$\beta = \tan^{-1} \frac{j \text{ intercept}}{i \text{ intercept}} = \tan^{-1} \frac{Y}{X}$$

$$\alpha = \tan^{-1} \frac{i \text{ intercept}}{k \text{ intercept}} = \tan^{-1} \frac{X}{Z}$$

$$\epsilon = \tan^{-1} \frac{k \text{ intercept}}{j \text{ intercept}} = \tan^{-1} \frac{Z}{Y}$$

Angeles $\phi$ and $\theta$ are derived using the law of cosines;

$$C_5^2 = A_5^2 + B_5^2 - 2A_5 B_5 \cos \phi$$

$$\phi = \cos^{-1} \frac{C_5^2 - A_5^2 - B_5^2}{-2A_5 B_5}$$

$$\phi = \cos^{-1} \frac{A_5^2 - C_5^2 - B_5^2}{-2A_5 B_5}$$

the length of l is:

$$l = \overline{C_5} \sin \phi.$$

Coordinates for point 75 can now be solved and for this example will be labeled from the standpoint of plane B. The angles and lengths of PD and DB, FIG. 10, are obtained as follows:

γ is obtained from triangle $C_2, C_{14}, C_{15}$ using the law of cosines;

$$\gamma = \cos^{-1} \frac{C_{14}^2 - C_{15}^2 - C_2^2}{-2C_{15}C_2}$$

ξ is obtained from triangle $C_2, D_{11}, D_{13}$ using the law of cosines;

$$\xi = \cos^{-1} \frac{D_{11}^2 - D_{13}^2 - C_2^2}{-2D_{13}C_2}$$

$$PD = D_{13} \sin(\gamma + \xi)$$

$$DB = D_{13} \cos(\gamma + \xi)$$

Figure 11:
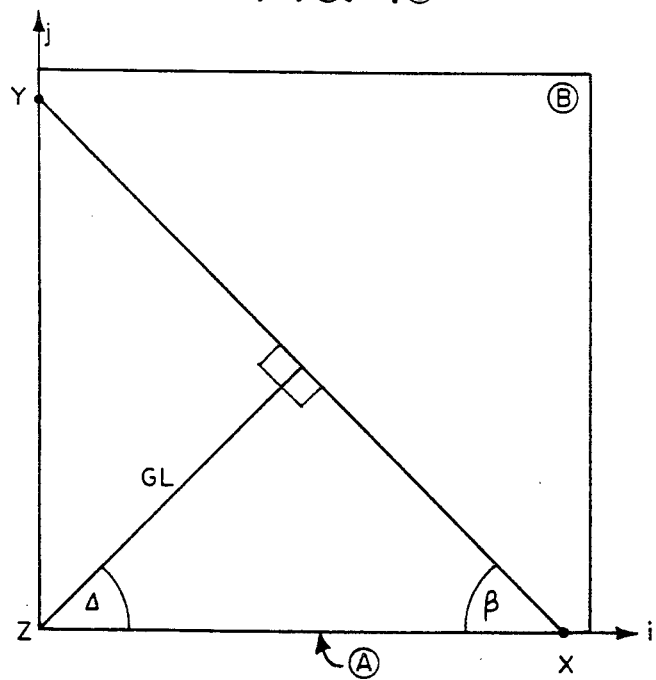

GL, FIGS. 9 and 11, is the apparent length of l, FIG. 9, in the projection, FIG. 11, onto plane B.

$$\Delta = 90° - \beta$$

$$GL = X_1 \cos \Delta$$

$$\Sigma(\text{FIG. 9}) = \sin^{-1} \frac{GL}{l}$$

Figure 12:
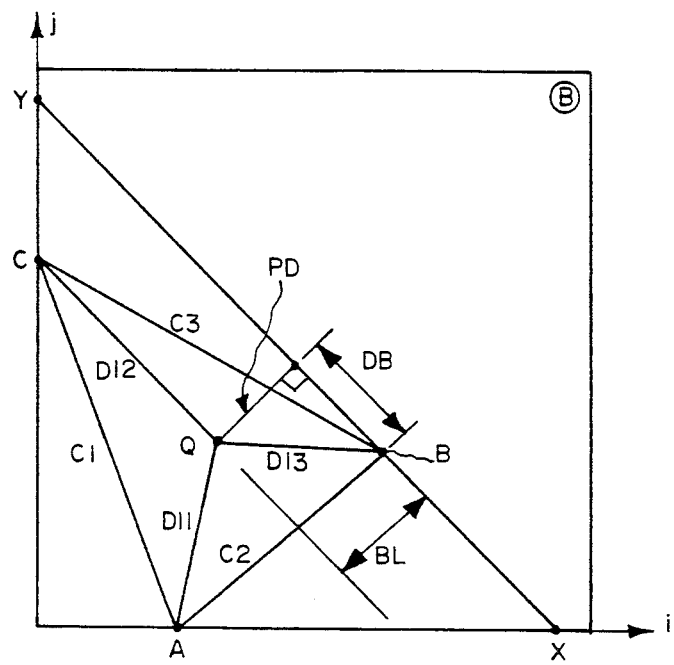
Figure 13:
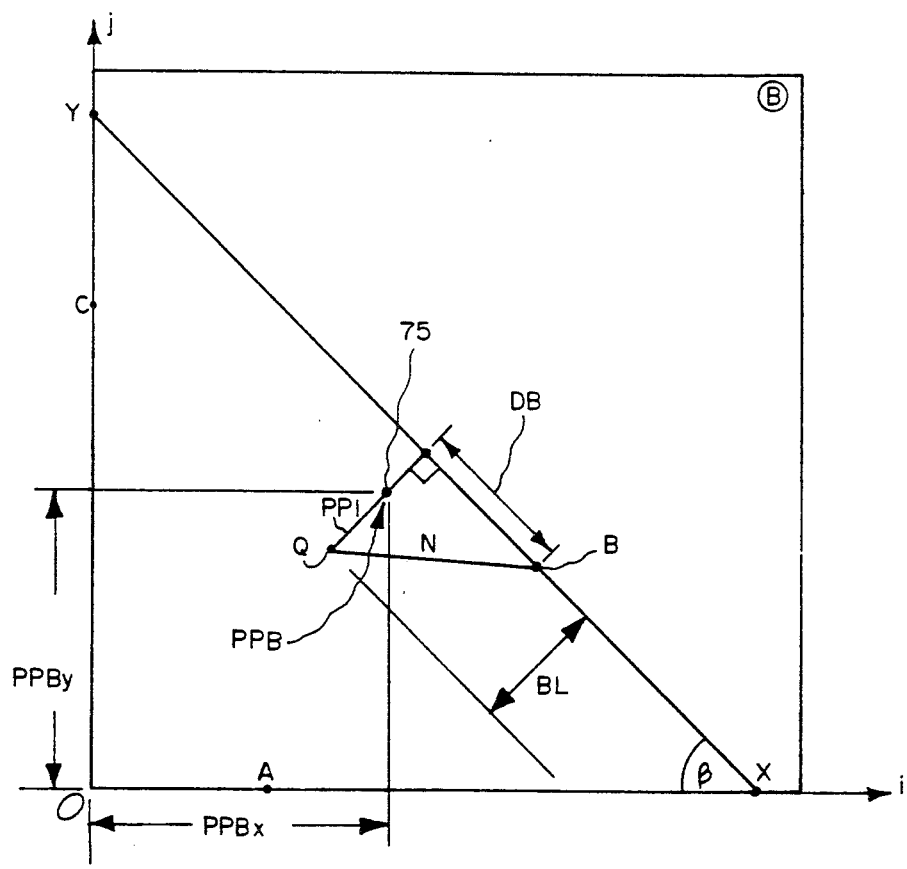

From the above, the position of point 75 (point P) and point Q in the various planes can be determined. FIGS. 12 and 13 show plane B, as does FIG. 11. In FIG. 12, the lines PD, $C_1, C_2, C_3, D_{11}, D_{12}$, and $D_{13}$ represent those lines in three dimensions projected onto plane B. Thus, the length of these lines are distorted and BL, the apparent length of line PD in plane B is not generally equal to the actual length of line PD. Referring to FIGS. 12 and 13, the apparent position of point 75 (point P) in plane B is given as follows:

$$BL = PD \sin \Sigma$$

$$N = \sqrt{DB^2 + BL^2}$$

The apparent length of $P_1$ in plane B, labeled $PP_1$, is given by:

$$PP_1 = P_1 \cos \Sigma.$$

The coordinates of point Q in plane B are:

$$Q_x = B_x - N \cos\left(90 - \beta + \tan^{-1}\left(\frac{DB}{BL}\right)\right)$$

$$Q_y = B_y - N \sin\left(90 - \beta + \tan^{-1}\left(\frac{DB}{BL}\right)\right)$$

The coordinates of point P in plane B, labeled PPB in FIG. 13, are:

$$PPB_Y = Q_y + PP_1 \sin(90 - \beta)$$

$$PPB_X = Q_x + PP_1 \cos(90 - \beta)$$

$$PPB_Z = \sqrt{P_1^2 - PP_1^2} + \frac{BL}{\tan \Sigma}$$

The equations have been solved to provide the three coordinates for point P with respect to plane B. The above equations assume all intercepts are positive. If one or more of the intercepts are negative, then an appropriate sign change in the appropriate equations for Q and PPB will be needed. To determine the apparent position of point P in the two dimensional plane B, only $PPB_x$ and $PPB_y$ are used. No movement or position in the Z direction can be seen in plane B. However, by solving for the position with respect to the x, y and z axes, the information is available to determine the apparent position not only in plane B, but also in planes A and C as well. For plane A:

$$PPA_X = PPB_X$$

$$PPA_Y = PPB_Z$$

$$PPA_Z = PPB_Y.$$

In the A plane, position in the Y direction is not seen. Thus, only $PPA_X$ and $PPA_Z$ are used.

For Plane C:

$$PPC_X = PPB_Z$$

$$PPC_Y = PPB_Y$$

$$PPC_Z = PPB_X.$$

In the C plane, movement in the X direction is not seen. Thus, only $PPC_Y$ and $PPC_Z$ are used.

The coordinates give the position of point P and the change in the coordinates of point P from one position to another, give the change in position of point P. There are several ways to determine and define the orientation of point P. To look at orientation and change of orientation with respect to a particular plane, the angle and change of angle of the base plane in the particular plane of observation can be determined. For this purpose, the orientation of the line in any plane of observation of the tetrahedron base plane may be used. For example, the angle β, FIGS. 9 and 11, indicates the orientation of point P in plane B. The angle α, FIG. 9, indicates the orientation of point P in plane A. The angle ε, FIG. 9, indicates the orientation of point P in plane C. The change in these angles from one measured position to a second measured position will indicate the relative rotation of the two points in each plane from the one position to the second.

In determining the movement from one position to another, if the position of point P has changed, and the angles, β, α, and ε remain the same, the relative movement is purely translational, if the position of point P remains the same, but one or more of the degrees β, α, and ε change, the relative movement has been rotational, if both positions and angles change, translational and rotational movement has occurred. If point P remains in the same position, and angles β, α, and ε have not changed, the positions of points A, B, or C must be looked at for each measured position to determine if no movement has occurred, or if rotation solely about $P_1$ as the axis has occurred. If points A, B, and C have moved, the amount of rotation can be determined from the extent of movement. Thus, with the parameters determined above, it is possible to determine the extent of any relative movement between points 75 (point P) and point 76.

Rather than looking at the rotation from one measured position to another in each individual plane, the rotation can be measured in relation to the line $P_1$. The direction or orientation of line $P_1$ will change if rotation of point P occurs. Thus, by determining the change in direction of $P_1$ from one measured point to another, the rotation that has occurred during movement between the two positions can be determined.

The various calculations required to determine relative positions and to keep track of relative movement of the two points, as well as all control functions for the apparatus, are performed by a calculation means which will usually take the form of a microprocessor or other computer system along with any required support components. As shown in FIG. 8, the detectors 28, 29, and 30, such as the charge coupled device arrays described, are connected to calculation unit 80. Position information is sent from the detectors to the calculation unit where they are stored in memory and as changes in position occur, calculations of the new position of point 75 with respect to point 76 are made. These can also be stored in memory. Also, various position and movement information as desired can be outputted from the calculation unit through various output devices 81, such as a CRT screen, printer, etc. The output can be done as the position and movement calculations are made, or the position and movement calculations can be made and stored, and can be outputted at any desired later time.

As described, the device of the invention provides information as to the relative positions and relative movement of two points, here points 75 and 76. In most instances, the points 75 and 76 will be attached to other items whose movement is to be measured. If only translational movement occurs between the two items for which relative movement is to be measured, the relative movement of the two points will generally be equal to the movement of the two items and the data indicating relative movement of the two points can be used directly. However, while the data obtained through the calculations as explained above indicates the amount of relative rotational movement as well as lateral movement that has occurred between the two points, which is the information required if completely unrestricted movement is to be measured, where rotational movement occurs, additional calculations may be necessary to relate the relative movement of the points 75 and 76 to the relative movement of the items for which movement is desired to be measured. This is because, as illustrated in FIGS. 1 and 2, the points 75 and 76 between which movement is measured are offset from the actual items about which such information is desired. Thus, while knowing that points 75 and 76 experience some rotational movement is valuable information and may be all the information required in some instances, it will usually be desirable to convert the movement measured between points 75 and 76 into a quantitative measurement of the actual rotational and translational movement experienced by the items to which the light source and sensor have been attached. Each particular measurement situation has to be addressed separately and the mathematics to relate the point movement to the item movement developed. This is because, for each situation, the reference point for defining movement has to be first chosen. Then the mathematics for relating measured movement of the two points to the reference determined. The mathematics used will then depend upon the distance of the points 75 and 76 from the reference point. Any rotational movement about the reference is amplified by the distance the points being measured are separated from and offset from the desired reference. Further, for any desired situation, such as measuring relative rotation of vertebra, there may be various reference points that could be used to reference the movement. The desired conversion can be done mathematically by the calculation means programmed appropriately for the situation, by other programmed computers, or, in some cases, may be easily done through use of a digitizer.

The present invention involves the determination of movement between two points, but the application of such information to particular circumstance is not part of the invention. For a description of how such information obtained from the invention can be applied to calculate movement of the vertebra with respect to one chosen reference of several that could be used, see the article entitled "A New Method for Assessing Relative Dynamic Motion of Vertebral Bodies During Cyclic Loading in Vitro" to be published in the *Journal of Biomechanics*. An advance copy of such article is submitted herewith and is incorporated by reference. It should also be noted that, depending upon the final information to be provided, the mathematics for determining the position and orientation of the two points as described above can be modified to suit the additional mathematics involved. Some modification is shown in the above referenced article.

The device as shown mounted on vertebra of a spinal column is used to measure the relative movement of vertebra upon various movements imparted to the spinal column by manipulation thereof. Such measurements are useful to determine the effectiveness of various spine immobilization devices. To test such devices, an immobilization device would be secured to appropriate vertebra in normal manner along with the apparatus of the invention. The spinal column is then manipulated and the device is used to determine and measure any resulting movement of the vertebra that were supposed to be immobilized. If more than an acceptable amount of movement occurs, the immobilization device is ineffective. A single light source and sensor has been shown and described as attached to adjacent vertebra, however, light sources and associated light sensors may be secured to any desired number of adjacent vertebra to provide detailed movement information for any desired number of vertebra. While the apparatus of the invention has been shown attached to spinal vertebra, the apparatus may be used anytime relative motion between two items or two parts of the same item is to be measured. For example, if motion between two items is to be measured, the light source is connected to one item and the sensor to the other item and the linkage adjusted so that the two units are arranged similarly as shown so the light beams fall on respective detectors. If motion between two portions of a single item is to be measure, such as two ends or portions of a beam under stress analysis, the light source is attached to one portion and the sensor to the other, and the linkage appropriately adjusted.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. Apparatus for measuring relative movement between two points, comprising radiation source means for generating three orthogonal radiation beams whose directional vectors intersect at a common point, said common point constituting one of said two points; radiation sensing means capable of detecting in three two dimensional sensing planes the position of each of three orthogonal radiation beams, said radiation sensing means arranged to detect in different planes the position of each of the three radiation beams from the radiation source means, each of said three sensing planes intersecting at an origin point, said origin point constituting the other of the said two points; and calculation means for calculating the relative position of the two points at a particular time from the determined positions of the three radiation beams striking the sensing means at that particular time.

2. Apparatus for measuring relative movement according to claim 1, wherein the sensing means includes three detectors, wherein each of the three detectors is capable of detecting in two dimensions the position of a radiation beam striking the detector, and wherein the three detectors are mounted in planes orthogonal to one another.

3. Apparatus for measuring relative movement according to claim 2, wherein the radiation source includes three separate radiation sources, each source generating one of the three radiation beams and each source arranged with respect to the other sources so that the radiation beam generated by each separate source appears to originate at the same point.

4. Apparatus for measuring relative movement according to claim 3, wherein the radiation sources are sources of light.

5. Apparatus for measuring relative movement according to claim 4, wherein the sources of light are laser diodes.

6. Apparatus for measuring relative movement according to claim 5, wherein the radiation sensing means are light sensing means.

7. Apparatus for measuring relative movement according to claim 6, wherein the light sensing means are light sensing arrays made up of a plurality of individual light sensing elements.

8. Apparatus for measuring relative movement according to claim 7, wherein the radiation sensing means are charge coupled device light sensing arrays.

9. Apparatus for measuring relative movement according to claim 7, wherein the radiation beams are of a diameter to encompass a plurality of individual light sensing elements, and the calculation means controls operation of the light sensing arrays and determines the positions of the radiation beams on the light sensing arrays by determining the position of the center of the radiation beam.

10. Apparatus for measuring relative movement according to claim 8, additionally including output means operatively coupled to the calculation means for providing output of the calculated relative position of the two points.

11. Apparatus for measuring relative movement according to claim 1, wherein relative movement between two items is to be measured, wherein the radiation source means is adapted to be attached to one of the items, and the sensing means is adapted to be attached to the other of the items.

12. Apparatus for measuring relative movement according to claim 11, wherein the radiation source means is adapted to be attached to one of the items through linkage, the sensing means is adapted to be attached to the other of the items through linkage, and the calculation means is adapted to compensate for the respective linkages to determine the relative positions of the two items.

13. Apparatus for measuring relative movement according to claim 1, wherein relative movement between two parts of an item is to be measured, wherein the radiation source means is adapted to be attached to one part of the item, and wherein the sensing means is adapted to be attached to the other part of the item.

14. Apparatus for measuring relative movement according to claim 13, wherein the radiation source means is adapted to be attached to one part of the item through linkage, and sensing means is adapted to be attached to the other part of the item through linkage, and the calculation means is adapted to compensate for the respective linkages to determine the relative position and orientation of the two parts of the item.

15. Apparatus for measuring relative movement according to claim 1, wherein the calculation means is adapted to calculate the relative position of the two points at a first relative position and at a second relative position and to additionally calculate the change in relative position of the two points from the first relative position to the second relative position.

16. Apparatus for measuring relative movement according to claim 15, additionally including output means operatively coupled to the calculation means for providing output of the calculated change in relative position of the two points from the first relative position to the second relative position.

17. A method of determining the relative unrestricted movement between a first and second point comprising, generating three orthogonal radiation beams whose directional vectors intersect at the first point; providing a sensing means capable of detecting radiation beams in three orthogonal two dimensional sensing planes, each of said three sensing planes intersecting at the second point; positioning the first point with respect to the second point so that respective radiation beams will fall on respective sensing planes over the expected extent of relative movement to be measured between the first and second points; determining the position where each of the radiation beams intersect respective sensing planes for a first relative position between the two points; determining the relative positions of the two points for that first relative position between the two points; determining the position where each of the radiation beams intersect respective sensing planes for a second relative position between the two points; and determining the relative position of the two points for that second relative position between the two points.

18. A method for determining the relative unrestricted movement between the first and second point according to claim 17, additionally including the step of determining the difference in position of the two points between the first relative position and the second relative position.

19. A method for determining the relative unrestricted movement between the first and second point according to claim 18, wherein the relative movement is expressed as relative movement in each of the three sensing planes.

20. A method for determining the relative unrestricted movement between the first and second point according to claim 19, wherein the relative movement is expressed as translational movement in each of the three sensing planes and as relative rotational movement.

21. A method for determining the relative unrestricted movement between the first and second point according to claim 20, wherein the relative rotational movement is expressed as rotational movement in each of the three sensing planes.

22. A method for determining the relative unrestricted movement between the first and second point according to claim 20, wherein the relative rotational movement is expressed as a single rotational movement.

23. A method for determining the relative unrestricted movement between the first and second point according to claim 17, wherein the position at each relative position of the two points is determined by treating the radiation beams as forming a right tetrahedron with apices defined by the first point and the points of intersection of the radiation beams with the sensing planes.

* * * * *